United States Patent [19]
Topham

[11] 3,977,235
[45] Aug. 31, 1976

[54] VISCOMETER

[75] Inventor: William Henry Topham, Rochester, England

[73] Assignee: The British Petroleum Company Limited, London, England

[22] Filed: Mar. 3, 1975

[21] Appl. No.: 555,035

[52] U.S. Cl. ................................................... 73/54
[51] Int. Cl.² ........................................ G01N 11/00
[58] Field of Search............. 73/54, 55, 343 R, 344, 73/345; 137/92, 90

[56] References Cited
UNITED STATES PATENTS

| | | |
|---|---|---|
| 2,597,138 | 5/1952 | Trigg.................................. 73/55 X |
| 3,025,232 | 3/1962 | Jones, Jr............................ 137/92 X |

*Primary Examiner*—Herbert Goldstein
*Assistant Examiner*—Joseph W. Roskos
*Attorney, Agent, or Firm*—Morgan, Finnegan, Pine, Foley & Lee

[57] ABSTRACT

An on-line monitoring device comprises a constant volume flow rate pump connected in series with a heater and a hydraulic resistance. A differential pressure transmitter is connected across the resistance and connected to a controller. The controller adjusts the power supply to the heater so that, in use, a predetermined differential pressure across the resistance is maintained. At least one temperature is associated with the hydraulic resistance.

9 Claims, 1 Drawing Figure

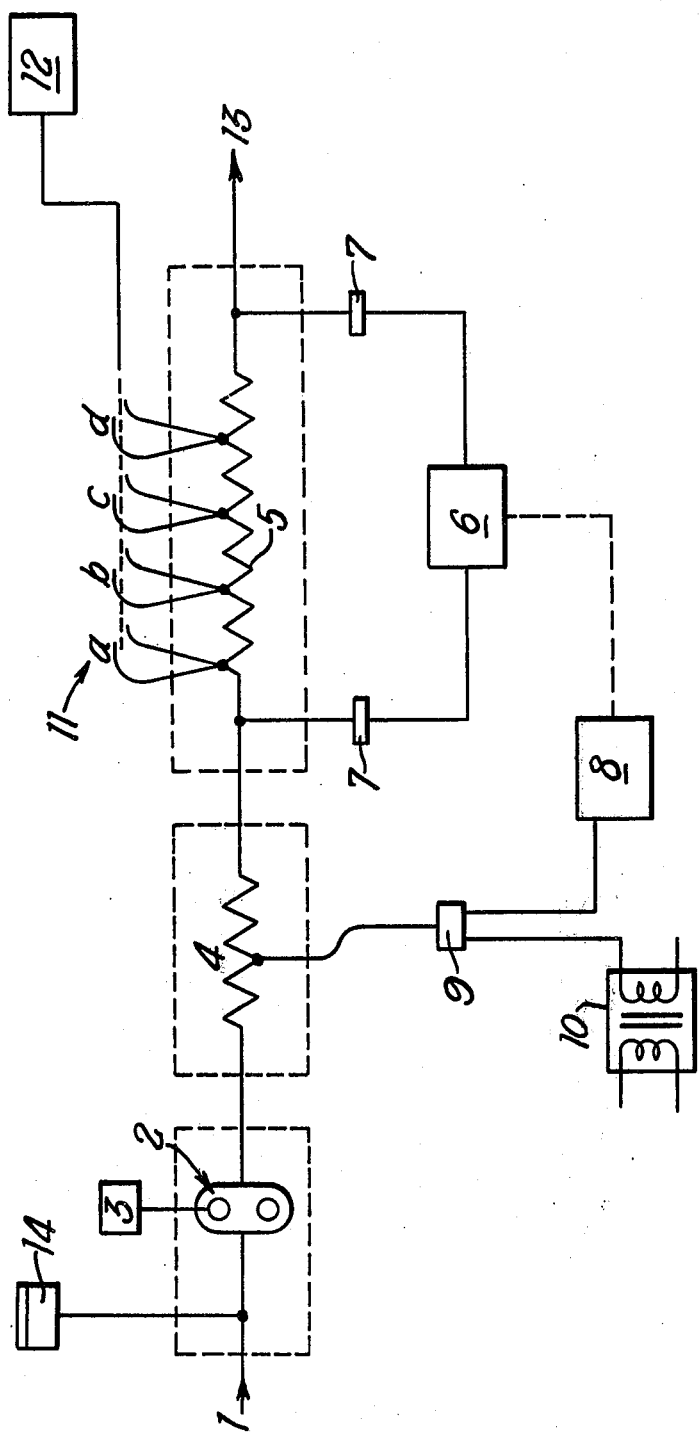

VISCOMETER

This invention relates to a monitoring apparatus.

There are many processes which are carried out in the petroleum industry in which the viscosity of the product is important, for example the production of fuel oils, either by blending or distillation. In order to control such a process it is necessary to measure the viscosity of the product and it is desirable to measure the viscosity as soon as possible after the product has been produced. This is achieved by continuously passing a portion of the product stream through an onstream monitor which continuously measures the viscosity or a related property.

It is known to measure the viscosity of a liquid by passing a sample under laminar flow conditions through a hydraulic resistance and measuring the volume flow rate through the pressure drop across the hydraulic resistance. The measurement of the volume flow rate is usually carried out by the use of a constant volume flow rate pump.

It is a feature of the operation of these viscometers that measurement is made at constant temperature e.g. in a thermostat bath. This operation at constant temperature is vital for application with products such as lubricating and fuel oils.

However in applications where a wide range of liquid viscosities are encountered particularly high viscosities e.g. bitumen grades, such viscometers are unsuitable both with regard to principle and practice for the purpose of on-line viscosity determinations.

It is an object of the invention to provide an apparatus suitable for the on-line monitoring of liquids having a wide range of higher viscosities, such as bitumens.

According to the invention, a monitoring apparatus comprises a constant volume flow rate pump operated by a prime mover, connected in series with a heater and hydraulic resistance, a differential pressure transmitter being connected across the resistance, the transmitter being connected to a controller adapted to adjust the power supplied to the heater so that, in use, a predetermined differential pressure across the hydraulic resistance is maintained, there being at least one temperature sensing device associated with the hydraulic resistance.

Preferably the pump is a precision metering pump.

Preferably the prime mover is a constant speed electric motor.

Preferably the controller is adapted to respond to an electrical signal from the differential pressure transmitter in such a manner that the power supplied to the heater enables a predetermined differential pressure to be maintained across the hydraulic resistance. Preferably the controller operates by proportional and integral control actions and most preferably by proportional, integral and derivative actions.

The heater is of low thermal inertia so that the temperature of the system may be varied rapidly to facilitate proper control. Preferably the system is heated electrically, the electrical power to the heater being regulated by the controller. Preferably the heater is constructed from stainless steel.

The hydraulic resistance is preferably a tube at least 50 cm., preferably 50–500 cm., in length and of circular cross section bore with an internal diameter of 2–5 mm. The hydraulic resistance is preferably coiled and should be of low thermal inertia. A suitable material for this purpose is stainless steel.

Preferably the differential pressure across the hydraulic resistance is measured with a conventional diaphragm-type differential pressure transmitter or by a strain gauge. Provided that suitable temperature ranges are used, other types of pressure measuring devices may be used.

Preferably the temperature sensing device is a thermocouple or a platinum resistance thermometer or a thermistor.

Preferably the output from the temperature sensing device is indicated and/or recorded.

For applications in which the liquid is of high viscosity, to avoid extensive heating of the lines to maintain liquid fluidity, a chemical seal may be placed between the liquid and the differential pressure transmitter. A suitable procedure is the use of a stainless steel diaphragm to transmit pressure from the working liquid to a seal liquid on the transmitter side. This procedure may be used for bitumen applications.

A monitoring apparatus according to the present invention is a flexible and reasonably compact instrument for the on-line monitoring or 'spot-checking' of liquids having a wide range of viscosities, particularly high viscosities e.g. bitumen, and will be suitable for operation in potentially hazardous areas e.g. oil installations.

The viscosity of bitumens is normally specified in terms of 'penetration value' i.e. the depth to which a special needle will sink into a sample of the bitument at 25°C under specified conditions. For the purpose of control this 'penetration value' can be related to the temperature at which the bitumen has a specified viscosity. Thus the apparatus described may be used to monitor the quality of bitumens.

In the operation of oil-fired boilers and heaters, it is necessary to provide the fuel to the burners at a specified viscosity to meet the demands of the burner design. For different grades of fuel it is necessary to heat the fuel to the 'burning temperature' i.e. the temperature at which the fuel has a specified viscosity. Thus the apparatus described may be used for the purpose of supplying fuel of specified viscosity to the burners of oil-fired burners and heaters.

The invention is illustrated with reference to the drawing accompanying the Provisional Specification which is a diagrammatic representation of the apparatus.

The sample enters the apparatus through line 1. All the apparatus must be kept at such a temperature that the sample remains fluid. This may be achieved by appropriate electrical heating. For bitumen measurements, a holding temperature of say 120°C is suitable and a lower temperature for other products. The sample then passes through a precision metering gear pump 2 driven at constant speed by a synchronous motor 3.

A low thermal capacity heater 4 is used to regulate the temperature of the sample before it passes into the measurement capillary 5 (hydraulic resistance). The stainless steel capillary 5 is typically 1 meter long and 3 mm. bore, coiled. It is of low thermal capacity so that a rapid response to temperature changes in sample is achieved. After passing through the measurement capillary 5 the sample leaves the viscometer by line 13.

The pressure across the capillary is measured by a conventional differential pressure transmitter 6. To prevent line blockage which may occur in the transmitter if there is a temperature drop flexible stainless steel diaphragms 7 are used as seals to transmit pressure from the working liquid to the seal liquid e.g. a silicone oil on the transmitter side.

The controller 8 received an electrical signal from the differential pressure transmitter 6, which is compared with the desired value. The controller 8 then regulates the power input to the heater 4 from the transformer 10 by on-off switching of the electrical current supply by device 9 to maintain zero error between the measured and desired value i.e. to maintain a pre-determined differential pressure and viscosity.

The average temperature of the oil in the capillary 5 is measured at this pre-set viscosity. This temperature is measured as the average value of four sensors (thermocouples) 11 (a–d) attached to the capillary 5.

A calibrated recorder 12 monitors the sample average temperature. A reservoir 14 of mobile oil e.g. lubricating oil is used for operating or flushing the system during standby, at shutdown or in event of a power or heating failure.

I claim:

1. A liquid monitoring apparatus comprising: a constant volume flow rate pump operated by a prime mover; said pump being connected in series with a heater and a hydraulic resistance; a differential pressure transmitter being connected across the resistance; the transmitter being connected to a controller adapted and arranged to adjust the power supplied to the heater in response to an electrical signal from the differential pressure transmitter in such a manner that the power supplied to the heater enables a pre-determined differential pressure to be maintained across the hydraulic resistance; at least one temperature sensing device connected with the hydraulic resistance to measure the temperature of the liquid, whereby the temperature of the liquid at a predetermined viscosity is monitored.

2. A monitoring apparatus according to claim 1 in which the pump is a precision metering pump.

3. A monitoring apparatus according to claim 1 in which the prime mover is a constant speed electric motor.

4. A monitoring apparatus according to claim 1 in which the hydraulic resistance is a tube at least 50 cm. in length, and of circular cross-section bore with an internal diameter of 2–5 mm.

5. A monitoring apparatus according to claim 4 in which the hydraulic resistance is of length 50–500 cms.

6. A monitoring apparatus according to claim 4 in which the hydraulic resistance is coiled and of low thermal inertia.

7. A monitoring apparatus according to claim 1 in which the differential pressure across the hydraulic resistance is measured with a conventional diaphragm-type differential pressure transmitter or by a strain gauge.

8. A monitoring apparatus according to claim 1 in which the temperature sensing device is a thermocouple or a platinum resistance thermometer or a thermistor.

9. A monitoring apparatus according to claim 1 in which the output from the temperature sensing device is indicated and/or recorded.

* * * * *